United States Patent [19]

Kurrle-Weitenhiller et al.

[11] Patent Number: 6,013,527
[45] Date of Patent: *Jan. 11, 2000

[54] PRESERVATIVE MIXTURE FOR DIAGNOSTIC TEST LIQUIDS

[75] Inventors: Angelika Kurrle-Weitenhiller, Tulzing; Axel Schmidt, München, both of Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/466,012

[22] Filed: Jun. 6, 1995

[30] Foreign Application Priority Data

Jun. 27, 1994 [DE] Germany .............................. 44 22 374

[51] Int. Cl.$^7$ ............................ A01N 43/40; A01N 43/80
[52] U.S. Cl. ................................ 436/18; 436/176; 422/61
[58] Field of Search ..................... 436/18, 176; 435/810, 435/963, 975; 252/380, 401, 405, 406; 422/61

[56] References Cited

U.S. PATENT DOCUMENTS

| | | | |
|---|---|---|---|
| 4,105,431 | 8/1978 | Lewis et al. | 71/67 |
| 4,824,957 | 4/1989 | Amick | 548/213 |
| 5,227,304 | 7/1993 | Wong | 436/18 |
| 5,283,005 | 2/1994 | Nelson, Jr. et al. | 252/380 |
| 5,300,424 | 4/1994 | Hoss et al. | 435/7.1 |

FOREIGN PATENT DOCUMENTS

| | | |
|---|---|---|
| 0 443 821 A1 | 8/1991 | European Pat. Off. . |
| 0 467 337 A2 | 1/1992 | European Pat. Off. . |
| 0 608 913 | 8/1994 | European Pat. Off. . |
| 3327485 | 2/1985 | Germany . |
| 2 077 915 | 1/1981 | United Kingdom . |
| 2 230 190A | 10/1990 | United Kingdom . |

*Primary Examiner*—Jeffrey Snay
*Attorney, Agent, or Firm*—Nikaido Marmelstein Murray & Oram, LLP

[57] ABSTRACT

A preservative mixture in particular for preserving diagnostic test liquids, contains the sodium salt of mercaptopyridine-N-oxide together with a further preserving substance. A diagnostic test kit according to the invention contains mercaptopyridine-N-oxide sodium salt, a compound from the isothiazolone group and in particular 2-alkyl-3-(2H)isothiazolone hydrochloride with 1 to 8 C atoms in the 2-alkyl group or a preservative mixture according to the invention as the preservative for one or several test liquids of the test kit.

15 Claims, No Drawings

PRESERVATIVE MIXTURE FOR DIAGNOSTIC TEST LIQUIDS

DESCRIPTION

The present invention concerns mixtures of preservatives the use of particular preservatives or preservative mixtures in test liquids of diagnostic test kits as well as diagnostic test kits in which one or several test liquids are stabilized with a preservative according to the invention.

It is not easy to find suitable preservatives for diagnostic test kits since the preservative frequently causes or may be expected to cause an impairment of the determination of the substance to be detected or quantified. A further problem is the low solubility of preservatives which even in the case of the previously known preservatives is not always adequate to enable an application in diagnostic test kits. Finally many of the previously known preservative substances have proven to be unsuitable since an increase in the turbidity of the reagent, interference in the recovery of samples, haemoglobin interference in samples containing blood, insufficient microbiological efficacy, instability of the reagent when stressed and other disadvantages have been observed. For these reasons sodium azide has preferably been used in diagnostic tests which up to now has at least exhibited the least interference with the tests and in particular with α-amylase tests.

However, the use of sodium azide is posing more and more problems. Nowadays one attempts to avoid the use of such toxic substances since sodium azide is a mutagenic, potentially carcinogenic and cytotoxic substance which in addition can also form explosive heavy metal azides on storage. Moreover the preservative action of sodium azide is sometimes problematic since resistances are on the increase and the activity spectrum is not very broad. In addition especially when an amylase test is carried out, a haemoglobin interference occurs which is caused by complex formation of haemoglobin with azide. This haemoglobin interference could only be partially eliminated by the addition of a substance which suppresses interference which, however, is also a disadvantage since this in turn introduces a further substance which itself can cause interferences etc.

The object of the present invention was therefore to provide a preservation which can be used especially in diagnostic tests while avoiding as far as possible interferences when carrying out the test.

This is achieved according to the invention by a preservative mixture, especially for preserving diagnostic test liquids, which contains the sodium salt of mercaptopyridine-N-oxide together with a 2-alkyl-3-(2H)isothiazolone hydrochloride, the 2-alkyl group of which comprises one to eight carbon atoms, or with a 2-bromo-2-nitropropanediol-1,3-derivative.

Surprisingly it turned out that the sodium salt of mercaptopyridine-N-oxide does not impair or impairs only to a negligible extent the diagnostic determination of particular substances in test liquids and in particular of α-amylase in body fluids. In addition mercapto-pyridine-N-oxide sodium salt is a compound which is only slightly toxic for higher organisms and its handling does not pose any problems at all.

When determining α-amylase using the preservative mixture according to the invention it turned out that the quality of the α-glucosidase used in the test is important. An α-glucosidase from a thermostable microorganism has proven to be particularly suitable.

A further advantage of the use of two preservatives in the preservative mixture according to the invention i.e. mercaptopyridine-N-oxide and one of the other above-mentioned preserving substances is that this prevents the development of resistances and that in general one can also manage with lower amounts of the respective substances.

A compound from the isothiazolone group is used as a further preserving substance in an embodiment of the present invention. In this connection 2-alkyl-3-(2H) isothiazolone hydrochlorides are preferred which contain 1 to 8 carbon atoms in the 2-alkyl group. A particularly preferred compound is 2-methyl-3-(2H)-isothiazolone hydrochloride (MIT) and also 2-methyl-4,5-trimethylene-4-isothiazolin-one.

In the case of a diagnostic amylase test a very much lower haemoglobin interference is observed particularly with one of these preferred preservative mixtures than when using sodium azide.

In an alternative embodiment of the invention a 2-bromo-2-nitropropanediol-1,3-derivative is used as a second preserving substance and particularly preferably bromonitrodioxane. Also in this preferred combination according to the invention only a slight haemoglobin interference occurs in amylase tests which is why in this case it is also possible to carry out the test without further measures to eliminate interference.

The individual substances of the preservative mixture are present in such amounts that they are preferably present in the test liquid to be preserved in the following concentrations: mercaptopyridine-N-oxide sodium salt: 0.005 to 0.1% and especially preferably 0.08 to 0.012%; isothiazolone compound 0.005 to 0.1% and especially preferably 0.015 to 0.025% as well as bromonitrodioxane 0.005 to 0.1% and especially preferably 0.015 to 0.025%.

The preservative mixture according to the invention thus has advantages in that it only causes very slight interferences in diagnostic tests and can therefore be used to preserve the liquids in diagnostic test kits without further measures to eliminate interference. Moreover it contains no compounds which are problematic with regard to their toxicity and, by combining at least two preserving substances, development of resistances is prevented and also relatively small amounts of the individual substances are adequate.

The present invention also concerns the use of mercaptopyridine-N-oxide sodium salt if desired together with a further preserving substance to preserve test liquids of diagnostic test kits. This subject matter of the invention is used in particular in an amylase test kit.

Further preserving substances that are preferred within the scope of the invention are those from the group comprising isothiazolones, preferably 2-alkyl- 3-(2H)isothiazolone hydrochloride the 2-alkyl group of which comprises one to eight carbon atoms and in particular 2-methyl-3-(2H)-isothiazolone hydrochloride (MIT) and also 2-methyl-4,5-trimethylene-4-isothiazolone as well as compounds from the group of 2-bromo-2-nitropropanediol-1,3-derivatives such as bromonitrodioxane in particular. The selection of further preserving compounds that can be used together with mercaptopyridine-N-oxide is within the scope of the skill of an expert; the mixture must be designed in such a way that it does not interfere with the intended test.

A compound from the group comprising isothiazolones and in particular 2-alkyl-3-(2H)isothiazolone hydrochlorides with 1 to 8 C atoms in the 2-alkyl group is, however, also particularly suitable for an application as a preservative in diagnostic test kits and in particular for an application in an amylase test which is why their corresponding use is also a further subject matter of the present invention. 2-Methyl- 3-(2H)-isothiazolone hydrochloride (MIT) and 2-methyl-4,5-trimethylene-4-isothiazolin-one are especially preferably used as compounds of the isothiazolone group.

The present invention also concerns diagnostic test kits which contain mercaptopyridine-N-oxide sodium salt or a compound of the isothiazolone group as a preservative for one or several test liquids of the test kit. In this connection 2-methyl-4,5-trimethylene-4-isothiazolin-one and 2-alkyl-3-(2H)isothiazolone hydrochloride with 1 to 8 C atoms in the 2-alkyl group and especially 2-methyl-3-(2H)-isothiazolone hydrochloride (MIT) are particularly preferred. In this connection mercaptopyridine-N-oxide can also be present in combination with an isothiazolone or with a 2-bromo-2-nitropropanediol- 1,3-derivative such as bromonitrodioxane in particular.

Such diagnostic test kits in turn represent a further subject matter of the present invention. The diagnostic test kit according to the invention which is preserved with the aid of the preservative mixture or the above-mentioned individual compounds according to the invention is particularly preferably a test kit for the determination of α-amylase. However, other test kits that use test liquids which are already present in the test kit in a liquid form and have to be stabilized over long periods are also suitable within the scope of the invention. The preservative mixture according to the invention can be used in all such diagnostic test kits and leads to the aforementioned advantages compared to previously known preservatives or methods for preserving liquids.

It is intended to further elucidate the present invention by the following examples.

Example 1
Solutions for the diagnostic determination of α-amylase

| Reagent 1: | α-glucosidase multifunctional: (Toyobo Company Japan) | 8 U/ml |
|---|---|---|
| | HEPES buffer: | 105 mmol/l pH 7.1 |
| | NaCl: | 52 mmol/l |
| | MgCl$_2$: | 10.5 mmol/l |
| | MIT or bromonitrodioxane | 0.02% |
| | mercaptopyridine-N-oxide, Na salt: | 0.01% |
| Reagent 2: | 4,6-ethylidene-G7-pNP: | 20 mmol/l |
| | HEPES buffer: | 105 mmol/l pH 7.1 |
| | NaCl: | 52 mmol/l |
| | MgCl$_2$: | 10.5 mmol/l |
| | MIT or bromonitrodioxane: | 0.02% |
| | mercaptopyridine-N-oxide, Na salt: | 0.01% |

Example 2
Procedure for the determination of the amount of α-amylase (total and pancreatic α-amylase)

Test principle 5 ethylidene-G7-pNP + H$_2$O $\xrightarrow{\alpha\text{-amylase}}$ ethylidene-G3 + G4-pNP + 2 ethylidene-G4 + 2 G3-pNP + 2 ethylidene-G5 + 2 G2-pNP G4-pNP + 2 G3-pNP + 2 G2-pNP + 14 H$_2$O $\xrightarrow{\alpha\text{-glucosidase}}$ 14 G + 5 pNP (G = glucose, pNP = Para-nitrophenol)

Pancreatic Amylase:

The salivary α-amylase is inhibited by specific antibodies so that only pancreatic α-amylase participates in the reaction described above.
Calibration: standard 1=0.9% NaCl, standard 2=Cfas
Quality control: PNU, PPU, PNE, PPE Sample material: serum, EDTA plasma, heparin plasma, urine
Dilution limit: 2000 U/l
Reagents:
    T-α-amylase: solution 1: enzyme solution, ready-to-use
        solution 2: substrate solution ready-to-use
    P-α-amylase: solution 1: enzyme antibody solution ready-to-use
        solution 2: substrate solution ready-to-use
Assay conditions: wavelength: Hg 405 nm
    cuvette: 1 cm path length
    measurement temperature: 37° C.
    measurement against air (increase in absorbance)

Pipette into a cuvette

| | Std 1 | Std 2 | Sample | QC |
|---|---|---|---|---|
| solution 1 | 2.5 ml | 2.5 ml | 2.5 ml | 2.5 ml |
| check measurement temperature | | | | |
| NaCl | 0.1 ml | — | — | — |
| Cfas | — | 0.1 ml | — | — |
| serum/plasma/uri | — | — | 0.1 ml | — |
| PNU/PPU/PNE/PPE | — | — | — | 0.1 ml |
| mix, incubate for 5 min at the measurement temperatur | | | | |
| solution 2 | 0.5 ml | 0.5 ml | 0.5 ml | 0.5 ml |
| mix, incubate at the measurement temperature | | | | |
| read A1 after exactly 3 min, A2 after exactly 6 min. | | | | |
| dA = A2 − A1 | | | | |

What is claimed is:

1. A diagnostic test kit, comprising at least one test liquid which is effective for the determination of alpha amylase, and further containing therein
    a sodium salt of mercaptopyridine-N-oxide and
    a 2-bromo-2-nitropropanediol-1,3-derivative as preservatives.

2. The diagnostic test kit as claimed in claim 1, wherein the 2-bromo-2-nitropropanediol-1,3-derivative is bromonitrodioxane.

3. The diagnostic test kit as claimed in claim 1, wherein the sodium salt of mercaptopyridine-N-oxide is present at 0.005 to 0.1%, and the 2-bromo-2-nitropropanediol-1,3-derivative is bromonitrodioxane, which is present at 0.005 to 0.1%.

4. The diagnostic test kit as claimed in claim 3, wherein the sodium salt of mercaptopyridine-N-oxide is present at 0.008 to 0.012%.

5. The diagnostic test kit as claimed in claim 3, wherein bromonitrodioxane is present at 0.015 to 0.025%.

6. A diagnostic test kit, comprising at least one test liquid which is effective for the determination of alpha amylase, and further containing therein a mercaptopyridine-N-oxide sodium salt and an isothiazolone as preservatives.

7. The diagnostic test kit as claimed in claim 6, wherein the isothiazolone is a 2-alkyl-3-(2H)isothiazolone hydrochloride, the 2-alkyl group of which contains one to eight carbon atoms.

8. The diagnostic test kit as claimed in claim 6, wherein the isothiazolone is selected from the group consisting of 2-methyl-3-(2H)-isothiazolone hydrochloride and 2-methyl-4,5-trimethylene-4-isothiazoline-one.

9. A method of preserving a test liquid which is effective for the determination of alpha amylase of a diagnostic test kit, comprising providing (a) a diagnostic test liquid, and (b) a preservative comprising a mercaptopyridine-N-oxide sodium salt and an isothiazolone, and combining (a) and (b) to produce a preserved diagnostic test liquid.

10. The method as claimed in claim 9, wherein the isothiazolone is selected from the group consisting of 2-methyl-3-(2H)-isothiazolone hydrochloride and 2-methyl-4,5-trimethylene-4-isothiazoline-one.

11. The method as claimed in claim 9, wherein the isothiazolone is a 2-alkyl-3-(2H)isothiazolone hydrochloride, the 2-alkyl group of which contains one to eight carbon atoms.

12. The method as claimed in claim 9, wherein the isothiazolone is 2-methyl-3-(2H)-isothiazolone hydrochloride.

13. A diagnostic test kit, comprising at least one test liquid which is effective for the determination of alpha amylase, and further containing therein as preservatives (a) 0.005 to 0.1% of a sodium salt of mercaptopyridine-N-oxide, and an additional component selected from the group consisting of
(b) 0.005 to 0.1% 2-methyl-3-(2H)-isothiazolone hydrochloride, 0.005 to 0.1% 2-methyl-4,5-trimethylene-4-isothiazolin-one and 0.005 to 0.1% bromonitrodioxane.

14. The diagnostic test kit as claimed in claim 13, wherein the additional component is 0.015 to 0.025% 2-methyl-3-(2H)-isothiazolone hydrochloride.

15. The diagnostic test kit as claimed in claim 13, wherein the additional component is 0.015 to 0.025% 2-methyl-4,5-trimethylene-4-isothiazolin-one.

* * * * *